US00PP29835P2

(12) United States Plant Patent
Vandenberg

(10) Patent No.: US PP29,835 P2
(45) Date of Patent: Nov. 13, 2018

(54) DENDRANTHEMA PLANT NAMED 'FIREDANCE IGLOO'

(50) Latin Name: ***Chrysanthemum* X *morifolium***
Varietal Denomination: Firedance Igloo

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 0 days.

(21) Appl. No.: 15/732,419

(22) Filed: Nov. 8, 2017

(51) Int. Cl.
*A01H 5/02* (2018.01)

(52) U.S. Cl.
USPC ..... Plt./286
CPC ..... *A01H 5/0255* (2013.01)

(58) Field of Classification Search
USPC ..... Plt./286
CPC ..... A01H 5/0255
See application file for complete search history.

*Primary Examiner* — Kent L Bell
(74) *Attorney, Agent, or Firm* — C. A. Whealy

(57) ABSTRACT

A new and distinct cultivar of *Dendranthema* plant named 'Firedance Igloo', characterized by its upright, outwardly spreading and uniformly mounded plant habit; freely branching habit; dense and full plant form; uniform and freely flowering habit; daisy-type inflorescences; bright greyed purple-colored ray florets; natural season flowering occurs about September 17 to 22 in Pennsylvania; and good garden performance and winter hardiness.

1 Drawing Sheet

Botanical designation: *Chrysanthemum* X *morifolium*.
Cultivar denomination: 'FIREDANCE IGLOO'.

BACKGROUND OF THE INVENTION

The present invention relates to a new and distinct *Dendranthema* plant, botanically known as *Chrysanthemum* X *morifolium*, commercially grown as a perennial garden-type *Dendranthema* plant, and hereinafter referred to by the cultivar name 'Firedance Igloo'.

The new *Dendranthema* is the product of a planned breeding program conducted by the Inventor in Bogota, Colombia and Smoketown, Pia. The objective of the breeding program is to create new perennial garden-type *Dendranthema* plants having uniformly mounding plant habit, inflorescences with desirable inflorescence forms, attractive ray and disc floret shapes and colors, winter hardiness and good garden performance.

The new *Dendranthema* plant originated from a cross-pollination made by the Inventor in 2008 in Bogota, Colombia, of a proprietary seedling selection of *Chrysanthemum* X *morifolium* identified as code number H7527, not patented, as the female, or seed, parent with *Chrysanthemum* X *morifolium* 'Cool Yoigloo', disclosed in U.S. Plant Pat. No. 20,225, as the male, or pollen, parent. The new *Dendranthema* plant was discovered and selected by the Inventor as a single flowering plant within the progeny of the stated cross-pollination in a controlled greenhouse environment in Smoketown, Pa. on Sep. 27, 2012.

Asexual reproduction of the new *Dendranthema* plant by terminal vegetative cuttings was first conducted in a controlled greenhouse environment in Smoketown, Pa. in March, 2013 and such asexual propagation has shown that the unique features of this new *Dendranthema* plant are stable and reproduced true to type in successive generations.

SUMMARY OF THE INVENTION

Plants of the new *Dendranthema* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Firedance Igloo'. These characteristics in combination distinguish 'Firedance Igloo' as a new and distinct garden-type *Dendranthema* plant:

1. Upright, outwardly spreading and uniformly mounded plant habit.
2. Freely branching habit; dense and full plant form.
3. Uniform and freely flowering habit.
4. Daisy-type inflorescences.
5. Bright greyed purple-colored ray florets.
6. Natural season flowering occurring about September 17 to 22 in Pennsylvania.
7. Good garden performance and winter hardiness.

In side-by-side comparisons, plants of the new *Dendranthema* differ from plants of the female parent selection primarily in ray floret color as plants of the female parent selection have coral red-colored ray florets. In addition, plants of the new *Dendranthema* are more outwardly spreading and flower later than plants of the female parent selection.

In side-by-side comparisons, plants of the new *Dendranthema* differ primarily from plants of the male parent, 'Cool Yoigloo', in the following characteristics:

1. Plants of the new *Dendranthema* are larger and more outwardly spreading than plants of 'Cool Yoigloo'.
2. Inflorescences of plants of the new *Dendranthema* are slightly larger than inflorescences of plants of 'Cool Yoigloo'.
3. Plants of the new *Dendranthema* and 'Cool Yoigloo' differ in inflorescence form and ray floret color as plants of 'Cool Yoigloo' have duplex/decorative type inflorescences with bright red purple-colored ray florets.

Plants of the new *Dendranthema* can be compared to plants of *Chrysanthemum* X *morifolium* 'Pumpkin Igloo', disclosed in U.S. Plant Pat. No. 27,001. In side-by-side comparisons, plants of the new *Dendranthema* differ from plants of 'Pumpkin Igloo' in the following characteristics:

1. Inflorescences of plants of the new *Dendranthema* are smaller than inflorescences of plants of 'Pumpkin Igloo'.
2. Plants of the new *Dendranthema* and 'Pumpkin Igloo' differ in ray flower color as plants of 'Pumpkin Igloo' have orange bronze-colored ray florets.

BRIEF DESCRIPTION OF THE PHOTOGRAPHS

The accompanying photographs illustrate the overall appearance of the new *Dendranthema* showing the colors as true as it is reasonably possible to obtain in colored reproductions of this type. Colors in the photographs may differ slightly from the color values cited in the detailed botanical description which accurately describe the colors of the new *Dendranthema* plant.

The photograph at the bottom of the sheet is a side perspective view of a typical flowering plant of 'Firedance Igloo' grown in a container.

The photograph at the top of the sheet is a close-up view of a typical flowering plant of 'Firedance Igloo'.

DETAILED BOTANICAL DESCRIPTION

The aforementioned photographs and following observations and measurements describe plants grown during the late summer and early autumn in 20-cm containers under full sunlight conditions in an outdoor nursery in Hermitage, Pa. and under cultural practices typical of commercial garden-type *Dendranthema* production. During the production of the plants, day temperatures averaged 26° C. and night temperatures averaged 15.6° C. Plants were 15 weeks old when the photographs and description were taken. In the following description, color references are made to The Royal Horticultural Society Colour Chart, 2007 Edition, except where general terms of ordinary dictionary significance are used.

Botanical classification: *Chrysanthemum* X *morifolium* 'Firedance Igloo'.

parentage:

*Female, or seed, parent.*—Proprietary selection of *Chrysanthemum* X *morifolium* identified as code number H7527, not patented.

*Male, or pollen, parent.*—*Chrysanthemum* X *morifolium* 'Cool Yoigloo', disclosed in U.S. Plant Pat. No. 20,225.

Propagation:

*Type.*—Terminal vegetative cuttings.

*Time to initiate roots, summer and winter.*—About two weeks.

*Root description.*—Fine, fibrous; typically white in color, actual color of the roots is dependent on substrate composition, water quality, fertilizer type and formulation, substrate temperature and physiological age of roots.

*Rooting habit.*—Freely branching, dense.

Plant description:

*Plant and growth habit.*—Perennial garden-type *Dendranthema* plant with daisy-type inflorescences; upright, outwardly spreading and uniformly mounding plant habit; strong and vigorous growth habit.

*Branching habit.*—Freely branching habit, primary lateral branches developing at potentially every node, each primary lateral with multiple secondary and tertiary branches; dense and full plant form; pinching is not required.

*Plant height, soil level to top of foliar plane.*—About 28 cm.

*Plant height, soil level to top of floral plane.*—About 30 cm.

*Plant width.*—About 51 cm.

*Lateral branches.*—Length: About 28 cm. Diameter: About 4 mm. Internode length: About 2.7 cm. Strength: Strong. Aspect: About 45° to 55° from vertical. Texture and luster: Pubescent, minute; longitudinally ridged; matte. Color: Developing, close to 148B to 148C; developed, close to 146A.

*Leaves.*—Arrangement: Alternate, simple. Length: About 5.2 cm. Width: About 5.4 cm. Shape: Ovate with rounded lobes. Apex: Broadly acute. Base: Truncate. Margin: Palmately lobed, medium sinuses between lateral lobes mostly parallel. Texture and luster, upper and lower surfaces: Pubescent, minute; veins prominent on lower surface; matte. Venation pattern: Pinnate. Color: Developing leaves, upper surface: Close to 146A. Developing leaves, lower surface: Close to 148A. Fully expanded leaves, upper surface: Close to N137A; venation, close to 147B. Fully expanded leaves, lower surface: Close to 147B; venation, close to 147C. Petioles: Length: About 1.8 cm. Diameter: About 2 mm. Texture and luster, upper and lower surfaces: Pubescent, minute; matte. Color, upper and lower surfaces: Close to 147B.

Inflorescence description:

*Type and arrangement.*—Daisy-type inflorescence form with elongated oblong-shaped ray florets; disc and ray florets arranged acropetally on a capitulum; inflorescences face mostly upright and held above, within and beyond the foliar plane on strong peduncles.

*Fragrance.*—Faintly fragrant; slightly sour.

*Flowering response.*—Under natural season conditions, plants flower about September 17 to 22 in Pennsylvania.

*Postproduction longevity.*—Inflorescences maintain good color and substance for about three to six weeks on the plant depending on temperatures; inflorescences persistent.

*Quantity of inflorescences.*—Freely flowering habit with about 32 inflorescences developing per lateral branch and more than 275 inflorescences per plant.

*Inflorescence buds.*—Height: About 1.1 cm. Diameter: About 1 cm. Shape: Ovoid. Texture and luster: Pubescent, minute; matte. Color: Close to 187B.

*Inflorescence size.*—Diameter: About 3.6 cm. Depth (height): About 1.7 cm. Disc diameter: About 1.2 cm. Receptacle diameter: About 1.2 cm. Receptacle height: About 5 mm.

*Receptacle shape.*—Rounded, shallow bowl-shaped.

*Receptacle color.*—Close to 148B.

*Ray florets*.—Quantity and arrangement: About 65 ray florets develop per inflorescence and arranged in about five whorls. Length: About 1.8 cm. Width: About 4 mm. Shape: Elongated oblong. Apex: Obtuse to shallowly emarginate. Base: Attenuate and then fused into a short tube. Margin: Entire. Orientation: Initially upright; with development, about 15° to 45° from horizontal; apices tend to curve upwardly. Texture and luster, upper and lower surfaces: Smooth, glabrous; longitudinally ribbed; matte. Color: When opening, upper surface: Close to 183A. When opening, lower surface: Close to 183C. Fully opened, upper surface: Close to 185A; venation, close to 185A; color becoming closer to 175B with development. Fully opened, lower surface: Close to 176C; venation, close to 176C; color becoming closer to 176D with development.

*Disc florets*.—Quantity and arrangement: About 156 fused disc florets develop per inflorescence, massed at the center of the capitulum and arranged in about ten whorls. Length: About 6 mm. Diameter: About 1.5 mm. Shape: Tubular, elongated. Apex: Five-pointed, acute apices. Texture and luster, inner and outer surfaces: Smooth, glabrous; matte. Color, developing, inner and outer surfaces: Close to 14A. Color, developed, inner and outer surfaces: Close to 12B; venation, close to 12B.

*Phyllaries*.—Quantity and arrangement: About 22 phyllaries develop per inflorescence and arranged in about three whorls. Length: About 7 mm. Width: About 2 mm. Shape: Elliptical. Apex: Acute. Base: Truncate. Margin: Entire; membraneous. Texture and luster, upper surface: Smooth, glabrous; glossy. Texture and luster, lower surface: Pubescent, minute; matte. Color, upper surface: Close to 146A. Color, lower surface: Close to 148B.

*Peduncles*.—Length, terminal peduncle: About 4.8 cm. Length, third peduncle: About 5.2 cm. Diameter, terminal peduncle: About 1 mm. Diameter, third peduncle: About 1 mm. Angle, terminal peduncle: Mostly upright. Angle, third peduncle: About 30° to 45° from stem axis. Strength: Strong. Texture and luster: Pubescent, minute; matte. Color: Close to 148B.

*Reproductive organs*.—Androecium (present on disc florets only): Stamen number: Five per floret. Filament length: About 2 mm. Filament color: Close to 1C. Anther length: Less than 1 mm. Anther diameter: About 2 mm. Anther shape: Narrowly oblong. Anther color: Close to 14A. Pollen amount: Scarce. Pollen color: Close to 15A. Gynoecium (present on ray and disc florets): Pistil length: About 6 mm. Stigma diameter: Less than 1 mm. Stigma shape: Bi-parted. Stigma color: Close to 15A. Style length: About 3 mm. Style color: Close to 1C. Ovary color: Close to 157C.

*Seeds and fruits*.—Seed and fruit production has not been observed on plants of the new *Dendranthema* to date.

Disease & pest resistance: Resistance to pathogens and pests common to *Dendranthema* plants has not been observed on plants of the new *Dendranthema* grown under commercial production conditions to date.

Garden performance & temperature tolerance: Plants of the new *Dendranthema* have demonstrated excellent garden performance, are hardy to USDA Zone 5 and tolerate high temperatures about 37.8° C.

It is claimed:

1. A new and distinct *Dendranthema* plant named 'Firedance Igloo' as illustrated and described.

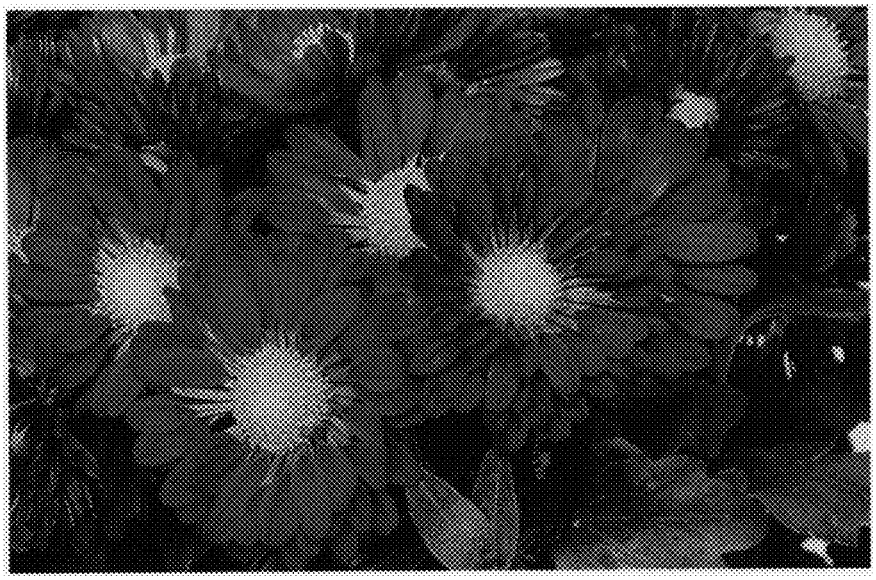
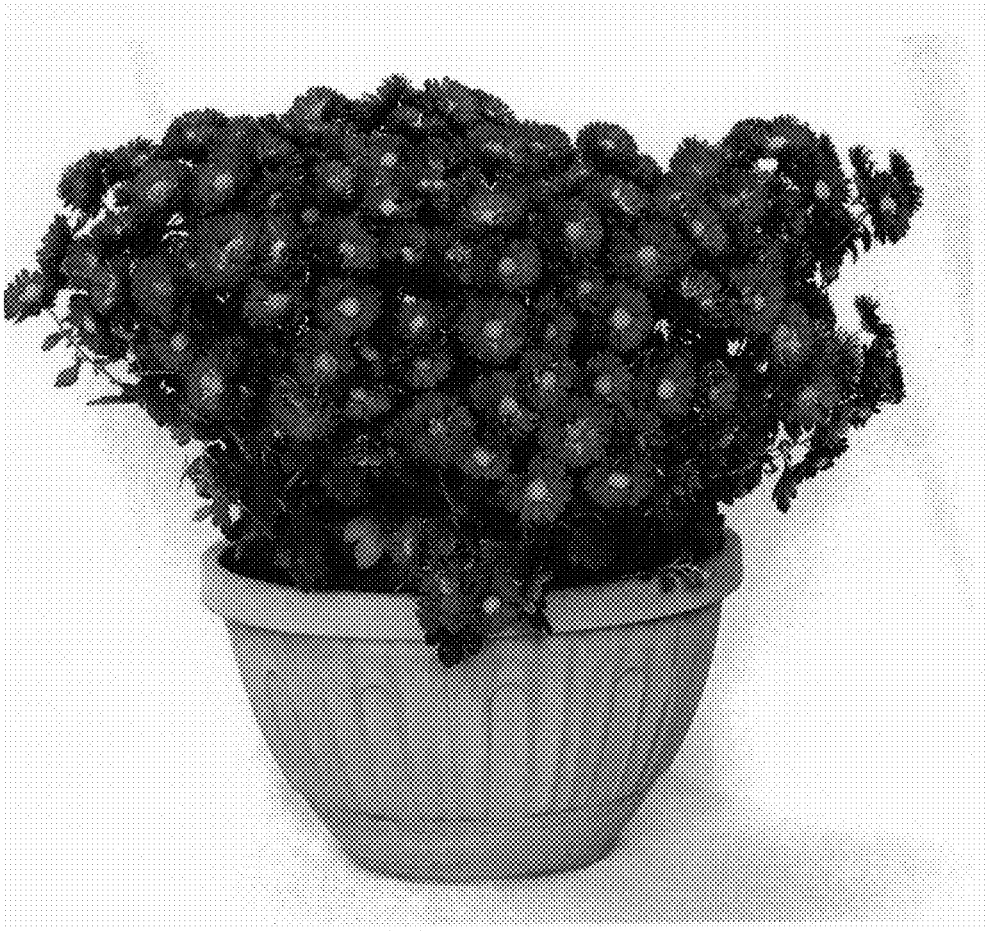

* * * * *